US011125727B2

(12) United States Patent
Zeqiri

(10) Patent No.: US 11,125,727 B2
(45) Date of Patent: Sep. 21, 2021

(54) ULTRASOUND SENSOR AND DETECTION APPARATUS

(71) Applicant: NPL Management Limited, Teddington (GB)

(72) Inventor: Bajram Zeqiri, Teddington (GB)

(73) Assignee: NPL Management Limited, Teddington (GB)

(*) Notice: Subject to any disclaimer, the term of this patent is extended or adjusted under 35 U.S.C. 154(b) by 0 days.

(21) Appl. No.: 16/456,147

(22) Filed: Jun. 28, 2019

(65) Prior Publication Data

US 2020/0408723 A1 Dec. 31, 2020

(51) Int. Cl.
*G01N 29/24* (2006.01)
*G01N 29/34* (2006.01)
(Continued)

(52) U.S. Cl.
CPC ......... *G01N 29/2431* (2013.01); *G01H 9/008* (2013.01); *G01N 29/348* (2013.01); *H01L 37/025* (2013.01); *A61B 8/0825* (2013.01)

(58) Field of Classification Search
CPC .. G01N 29/2431; G01N 29/348; G01H 9/008; H01L 37/025; A61B 8/0825
See application file for complete search history.

(56) References Cited

U.S. PATENT DOCUMENTS 5,396,143 A * 3/1995 Seyed-Bolorforosh ...................... H01L 41/08
310/334
6,978,677 B2 * 12/2005 Bajram .................... G01H 3/10
73/646

(Continued)

FOREIGN PATENT DOCUMENTS

EP 2378975 A2 10/2011

OTHER PUBLICATIONS

"Unidimensional Modeling of Multi-Layered Piezoelectric Transducer Structures" by David J. Powell, Gordon Hayward, and Robert Ting—IEEE transactions on ultrasonics, ferroelectrics and frequency control, vol. 45, No. 3, May 1998 (Year: 1998).*

(Continued)

*Primary Examiner* — Herbert K Roberts
*Assistant Examiner* — John M Royston

(57) ABSTRACT

A sensor or receiver array includes first and second pyroelectrically active electrodes formed of polyvinylidene difluoride and separated by a spacer layer that acts to electrically separate the pyroelectric layers while keeping them close enough such that they see effectively the same vibration or background acoustic excitation while maintaining sufficient separation to ensure that they generate significant differences in their pyroelectric responses. The structure provides two distinct signals (at separate timestamps), the difference between which provides a more accurate signal. An ultrasound detection system includes the tri-laminar sensor, disposed within a detection zone in which a test element can be positioned. The apparatus includes a processing unit, which comprises a detector unit coupled to the first and second pyroelectric elements and configured to derive a differential signal from the first and second pyroelectric elements. A processor is coupled to the detector unit and is configured to generate an electrical output waveform on the basis of the data extracted from first and second pyroelectric elements.

16 Claims, 6 Drawing Sheets

(51) Int. Cl.
  *H01L 37/02* (2006.01)
  *G01H 9/00* (2006.01)
  *A61B 8/08* (2006.01)

(56) References Cited

U.S. PATENT DOCUMENTS

| | | | | |
|---|---|---|---|---|
| 2002/0117695 A1* | 8/2002 | Borges | H01L 23/3735 | 257/279 |
| 2012/0010510 A1* | 1/2012 | Zeqiri | A61B 8/00 | 600/459 |
| 2012/0198937 A1* | 8/2012 | Kajitani | G01H 5/00 | 73/597 |
| 2014/0152016 A1* | 6/2014 | Jennings | F03G 7/08 | 290/55 |
| 2014/0375171 A1* | 12/2014 | Tai | B06B 1/0622 | 310/341 |
| 2015/0071468 A1* | 3/2015 | Chiang | H04R 19/00 | 381/191 |
| 2020/0194653 A1* | 6/2020 | Mainguet | H01L 37/02 | |

OTHER PUBLICATIONS

Extended European Search Report for Application No. 19275082.6 (dated Nov. 22, 2019).
Powell et al., "Unidimensional Modeling of Multi-Layered Piezoelectric Transducer Structures," IEEE Trans. on Ultrasonics, Ferroelectrics and Frequency Control, vol. 45, No. 3 (May 1998).
Robinson et al., "PVDR Reference Hydrophone Development in the UK—from Fabrication and Lamination to Use as Secondary Standards," IEEE Trans. on Ultrasonics, Ferroelectrics, and Frequency Control, vol. 47, No. 6 (Nov. 2000).
Schoenwald, "Strategies for Robotic Sensing Using Acoustics," IEEE 1985 Ultrasonics Symposium (Oct. 16, 1985).
Chuang et al., "Ultrasonic Tactile Sensor Integrated with TFT Array for Contact Force Measurements," 2017 19th Int'l Conf. on Solid-State Sensors, Actuators and Microsystems (Transducers), IEEE (Jun. 18, 2017).
Zeqiri et al., "Systematic Evaluation of a Secondary Method for Measuring Diagnostic-Level Medical Ultrasound Transducer Output Power Based on a Large-Area Pyroelectric Sensor," Metrologia, Inst. of Physics Publishing, Briston, GB, vol. 49, No. 3 (Apr. 25, 2012).
Baker et al., "Pulse Pileup Correction of Signals from a Pyroelectric Sensor for Phase-Insensitive Ultrasound Computed Tomography," IEEE Trans. on Instrumentation and Measurement, vol. 68, No. 10 (Oct. 2019).

\* cited by examiner

ULTRASOUND SENSOR AND DETECTION APPARATUS

TECHNICAL FIELD

The present invention relates to ultrasound sensors and transducers and to detection apparatus using such sensors and transducers. The detection apparatus may be designed for tissue screening, in particular but not limited to screening for breast disease. The teachings could also be used to detect the structural characteristics of other three-dimensional structures, such as submerged pipes to inspect the contents, typically in the presence of a coupling medium such as water between the sensor array and the structure undergoing detection.

BACKGROUND ART

Medical imaging, including ultrasound imaging, is an important diagnostic tool of increasing usage in the analysis of a variety of medical conditions.

For example, each year more than two million women have breast cancer screening in the UK, and more than 18,000 breast cancers are diagnosed through screening in England each year. Over 55,000 women are diagnosed with invasive breast cancer each year in the UK, while 11,500 women die each year from the disease. A 2013 review published in The Breast suggested that 25-46% of women failed to re-attend screenings as a result of pain experienced while undergoing previous mammograms.

Current mammograms typically use X-ray based mammography (XRM) technologies: 2D full-field digital mammography (FFDM) or 3D digital breast tomosynthesis (DBT) technology, both of which involve exposure to ionising radiation. The level of radiation used in a mammogram is of course kept well within background radiation levels and no conclusive evidence linking mammograms and breast cancer has been found. Nonetheless, screening methods that do not involve radiation are recommended best practice by the UK National Health Service (such as MRI scanners). However, the main non-ionising radiation option, MRI, is substantially more expensive (£2 million to £4 million per MRI suite) and waiting times are longer.

Traditional ultrasound is frequently used as an adjunct to XRM, particularly for screening women with dense breasts, where ultrasound provides much better contrast. Breast density in younger women and women of Asian backgrounds is particularly problematic. XRM devices are poor at differentiating between cancerous tissue (which has high density) and breast tissue that is normal but naturally dense. Having dense breasts also significantly increases the chance of developing breast cancer.

In common with 2D x-ray mammograms, both FFDM and DBT involve breasts being compressed between two plates and being pulled away from the body. This is uncomfortable for many women.

Compression can also cause overlapping of breast tissue, with the result that cancerous tissue can be caught in the overlaps and overlooked (false negative), which can be a problem in FFDM. Overlaps can also cause false positives due to pseudolesion or summation artefacts. This overlap occurs because detection of the digital signal depends on the total attenuation of the x-ray beam by the intervening tissue.

Mammograms also give only a limited range of angles of image. In order to obtain images at different angles it is necessary to obtain additional images, subjecting the patient to proportionately greater radiation doses.

The current state of the art is 3D digital mammography ("Digital Breast Tomosynthesis" DBT), which uses 1-mm single-section images and enables 3D images of breasts. However, DBT still requires compression of breasts and therefore still causes patient discomfort. Moreover, DBT devices are expensive at more than $400,000 each, compared with around $200,000 for 2D devices.

Ultrasound Computed Tomography of soft tissues, should in principle be a powerful tool for detecting disease onset, particularly for the breast where through-transmission can be used. Despite research activity spanning 30 years, its full potential has yet to be realised. This is due to imaging artefacts which affect image quality and compromise achievable resolution. These limitations arise directly from the phase-sensitive nature of the sensors used, and the way inhomogeneities in tissue speed of sound refract and diffract the acoustic wave, altering the phase distribution. It has been shown that sensors or transducers which response to acoustic power or time-averaged ultrasound intensity greatly reduce these artefacts, allowing quantitative images of ultrasound attenuation to be derived which can potentially be linked to tissue pathology. Sensors operating on pyroelectric principles are an example of such a phase-insensitive sensor, as described for example in the applicant's earlier EP-2,378, 975 and in Quantitative ultrasonic computed tomography using phase-insensitive pyroelectric detectors, Zeqiri, B; Baker, C; Alosa, G; Wells, P N T; Liang, H D; PHYSICS IN MEDICINE AND BIOLOGY, Vol 58, Issue 15, 2013. As shown, the pyroelectric elements are in a common plane.

However, these pyroelectric sensors operate on the basis of a thermal response to an applied acoustic excitation energy, which is inherently "slow". Response times can be made faster by looking at signals immediately after switch on of the ultrasound radiation. This can be commonly achieved through interfacing of the sensor with an electronic detection module of appropriate electrical input impedance, which acts as a high pass filtering of the signal generated by the pyroelectric sensor. This reduces the signal considerably and is realised in an overall detector system which is very sensitive to its environment, in particular signals from vibration and acoustic signals. This sensitivity to vibration and acoustic signals comes from the fact that pyroelectric materials used in the sensors also have a piezoelectric response. Signals generated by the pyroelectric and piezoelectric mode of operate overlap in terms of frequency range (essentially for frequencies up to 10 kHz). Additionally, the generated pyroelectric signals can be affected by stray radio-frequency electrical radiation.

Further sensors are disclosed in US 2014/0269206 A1, AU 2003204147 A1, CN 106679793 A1, JP S6226240 B2, U.S. Pat. Nos. 4,627,138, 5,153,859, 6,452,310, 7,602,108 and 8,840,559 and in the articles "Transduction Mechanisms of the Fabry-Perot Polymer Film Sensing Concept for Wideband Ultrasound Detection", IEEE Transactions on Ultrasonics, Ferroelectrics, and Frequency Control, Vol. 46, No. 6, November 1999; and "Design Considerations for Piezoelectric Polymer Ultrasound Transducers", IEEE Transduction on Ultrasonics, Ferroelectrics, and Frequency Control, Vol 47, No. 6, November 2000.

SUMMARY OF THE INVENTION

The present invention seeks to provide an improved ultrasound sensor and improved imaging apparatus.

According to an aspect of the present invention, there is provided an ultrasonic sensor including first and second overlaying pyroelectric layers and an electrically insulating spacer layer disposed between the first and second pyroelectric layers so as to separate electrically the first and second pyroelectric layers from one another.

In use, the first and second pyroelectric layers act respectively as a measurement electrode and as a reference electrode.

The skilled person will appreciate that in practical implementations arrangement of the sensor may be in a vertical or quasi-vertical arrangement while in others may be in a lateral arrangement.

The first pyroelectric layer is advantageously in intimate, direct, contact with an absorbing layer which is exceedingly absorbing to ultrasound energy at the generated frequency. In practice, following transmission through the first (measurement) pyroelectric layer, the majority of the acoustic power is absorbed within a millimetre or so of the pyroelectric layer, leading to heat being generated which dissipates across the various sensor layers.

The spacer layer preferably has a thickness of no more than 100 micrometres, typically of between 1 and 100 micrometres, and most preferably of around 9 micrometres. In practice, the spacer layer has a minimum thickness that achieves electrical isolation between the first and second pyroelectric layers; that is so as to enable the first and second pyroelectric layers to be subjected to substantially the same background acoustic and vibration excitation while providing different pyroelectric responses. The first and second pyroelectric layers in use provide differential signals in response to the ultrasonic excitation energy.

The spacer layer is preferably made of a polymer material, such as polyethylene terephthalate, a polyester or polymethyl methacrylate. This is a preferable characteristic in the described embodiment because of the use of a polymer as the piezo/pyroelectric layer to reduce losses due to acoustic reflections from the various layers. For optimum performance it is important to match the acoustic impedance (Z=density×speed of sound) of the various layers as much as possible so as not to reduce the sensitivity or have ultrasound reflections. The indicated materials provide a good match to PVDF in terms of Z. However, for a pyroelectric layer made of a ceramic, for example, possibly sprayed onto a thin supporting membrane, a different spacer layer may be preferable.

Advantageously, the spacer is made of thermally conductive material.

The sensor may include at least one signal dissipating layer disposed in contact with at least one of the pyroelectric layers, or the spacer. The purpose of the signal dissipating layer is to seek to dissipate heat completely before it reaches the second (reference) electrode, which would then only respond to background disturbing effects such as electrical pick-up, acoustic and vibrational noise. This can increase the amplitude of the differential signal. With the advent of graphene and carbon nanotubes, it is considered possible to deposit very thin layers onto the first membrane, either at the absorber surface or next to the spacer (or onto the spacer itself to boost this lateral dissipation of heat). This can assist in making the response of the sensor faster.

A heat sink is advantageously coupled to the first pyroelectric layer for removing heat from said pyroelectric layer, in accordance with the teachings given herein.

The first and second pyroelectric layers may each have a thickness of substantially 28 micrometres, typically of between 1 and 60 micrometres.

In the preferred embodiments, the first and second pyroelectric layers are made of polyvinylidene difluoride, which is well matched in terms of Z (acoustic impedance) to the water medium used to transmit the ultrasound. This reduces any reflection and loss of sensitivity of the sensor.

According to another aspect of the present invention, there is provided ultrasound detection apparatus including: a generator of ultrasound energy; at least one ultrasound transducer comprising first and second overlaying pyroelectric layers separated by an electrically insulating spacer layer; a detector unit coupled to the first and second pyroelectric layers and configured to derive a differential signal from the first and second pyroelectric layers; and a processor coupled to the detector unit and configured to generate a detection profile on the basis of the differential signal.

Other aspects and features of the disclosure herein will become apparent from the following the description of the preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There is described herein a new structure of ultrasound receiver array (transducer) able to provide phase insensitive ultrasound detection for use in a variety of ultrasound apparatus and particularly applicable to the medical field, for example in breast cancer screening using Ultrasound Computed Tomography. The receiver structure could be described as being a tri-laminar array formed of first and second pyroelectric layers separated by a spacer. The skilled person will appreciate that the structure includes a number of other layers that provide ancillary functions to the three layer core structure.

Figure 1:
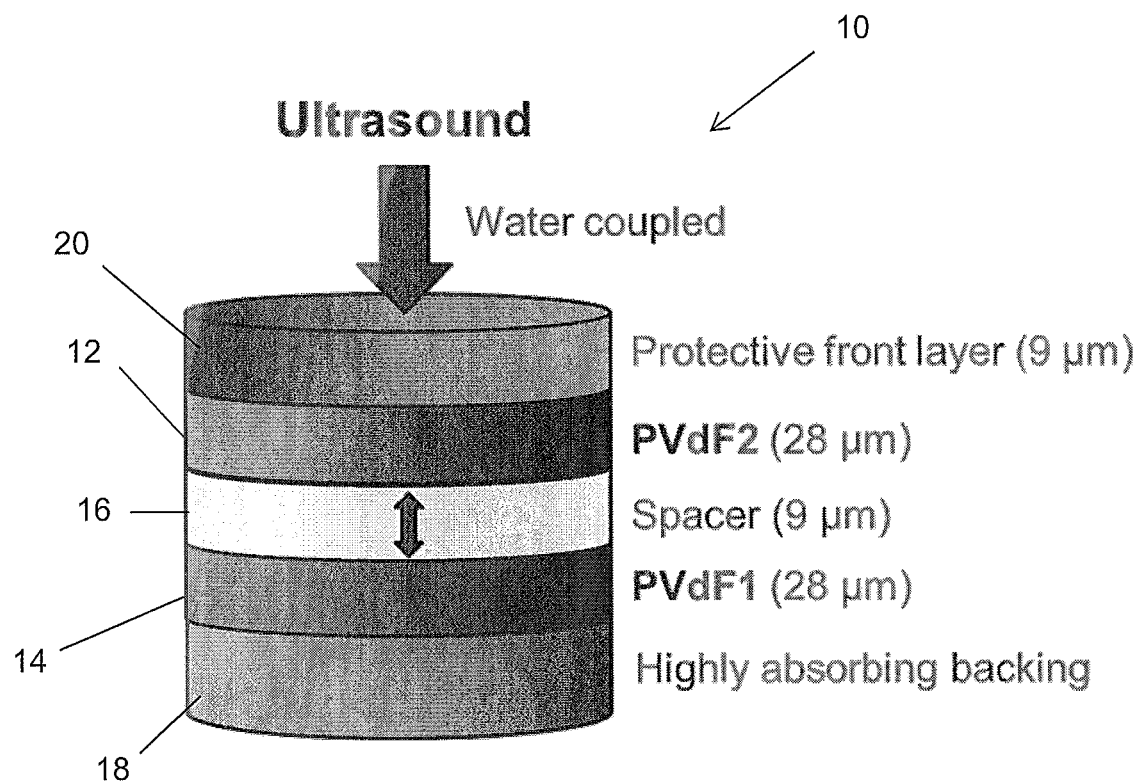
FIG. 1 shows in schematic form a preferred embodiment of ultrasound transducer in accordance with the teachings herein.

Referring to FIG. 1, this shows a preferred embodiment of receiver array or transducer 10, which includes first and second pyroelectric electrodes 14, 12 preferably formed of poled polyvinylidene difluoride (PVDF). The pyroelectric layers 14, 12 in this embodiment have a thickness of 28 micrometres, although may in other embodiments have a thickness anywhere in the range from 1 to 60 micrometres. The thickness of the pyroelectric layers 14, 12 is typically dependent upon the nature of the material used for these layers and upon the pyroelectric characteristics desired for the detector. Thinner layers 12 and 14 can provide greater gains in peak amplitude and reduced time to peak due to more rapid heat diffusion through the material of the layer. PVDF layers that are too thick can lead to higher reflections and reduced sensitivity.

The first and second pyroelectric electrode layers 14, 12 are in the preferred embodiments identical in constitution (material) and size (thickness and volume). This ensures that the signals from the first and second pyroelectric elements are directly comparable. The skilled person will appreciate, however, that in other embodiments the first and second pyroelectric layers 12, 14 may be different, for example to be of different size (e.g. thickness) or material, in which case it is preferred that the detection apparatus is configured to calibrate the signals from the first and second pyroelectric elements so as to produce a reliable and usable differential signal therefrom.

In the case where the two electrodes are precisely the same, it is envisaged that one could reverse the polarity of the two signals (by flipping one of the membranes around) and sum their outputs directly to derive a difference signal. In practice, it is advantageous to be able to monitor the signals separately (as well as the differential or summation) as this can provide diagnostic information about how good any particular measurement is during the scan to reduce artefacts.

Disposed between the first and second pyroelectric electrode layers 14, 12 is a spacer layer 16 that acts:

1) to electrically separate the pyroelectric layers 12, 14; and
2) to keep the two pyroelectric layers 12, 14 close enough such that they see effectively the same vibration or background acoustic excitation; while
3) maintaining sufficient distance to ensure that the pyroelectric layers 12, 14 generate significant differences in their pyroelectric responses.

The first on lower pyroelectric electrode layer 14 is disposed adjacent the absorbing highly backing layer 18, which acts as the heat source.

This structure provides two distinct signals (at separate timestamps), the difference between which provides a more accurate signal. The spacer layer 16 of the embodiment of transducer 10 shown in FIG. 1 has a thickness of 9 micrometres, which has been found particularly effective in tests, although could have a thickness from 1 to 100 micrometres. The spacer 16 may be made of polyethylene terephthalate, another polyester such as Mylar (Registered Trade Mark), polymethyl methacrylate, or any other suitable polymer in the case of electrodes formed, for example, of PVDF. For electrode layers made of other materials, the spacer layer could likewise be made of a different material, as explained above. The spacer 16 provides electrical separation between the first and second pyroelectric layers 14, 12 but is preferably heat conductive (most preferably being substantially transparent to heat). In some embodiments the spacer layer 16 may be made of polyvinylidene fluoride (PVDF). This configuration provides the best acoustic impedance match as is same as the material either side. The spacer layer has been formed as an unpoled layer so as not to be piezo or pyroelectrically active. Poling is the process which essentially lines up the molecules so that the material responds to changes in pressure and temperature.

There is an optimum thickness for the spacer layer 16. Specifically, the inventor has discovered that too thick a spacer layer has a deleterious effect on the directional response of the sensor, that is the way the output of the device responds to ultrasound striking the surface of the device at an angle (rather than perpendicularly). The preferred device should be omnidirectional, such that at whatever angle the ultrasound is incident, the output of the device should be the same. Spacers of up to 100 micrometres in thickness can greatly enhance the response to non-perpendicular incidence and as a consequence tissue imaging, while significant departures from this thickness will adversely affect tissue reconstructions for Ultrasound Computed Tomography. Too thin a spacer layer 16 can result in the pyroelectric response of the two layers 12, 14 being very similar to one another, such that differential operation will reduce the output voltage waveform and therefore the sensitivity of the device. Tests to date have shown that the optimum thickness of the spacer layer is in the region of 9 micrometres. The sensor structure 10 also includes a high energy absorbency base or backing layer 18 for boosting sensor sensitivity. A suitable material for the backing absorber is based on a di-functional polytetramethylene glycol. In order to achieve significantly increased absorption above that of the base material, small micro-balloons of the material Expancel® may be used. Additionally, in order to modify the acoustic impedance of the backing material so that it is better matched to water, a high-density filler may be added to increase the material density to a value of 1,910 kg m$^{-3}$. The absorption coefficient of the material at 3 MHz is preferably greater than 950 dB cm$^{-1}$.

The absorbing layer 18, with which the first pyroelectric layer 14 is preferably in direct, or intimate, contact, is very absorbing of ultrasound energy at the generated frequency. In practice, following transmission through the first pyroelectric layer 14, the majority of the acoustic power is absorbed within a millimetre or so of the pyroelectric layer, leading to heat being generated which dissipates across the various sensor layers.

There is preferably also provided a protective layer 20 disposed so as to overlie the top of the array 10, which is transparent to ultrasound and made of electrically insulating and preferably water impermeable material. This may be of the same material as the spacer layer, although in the preferred embodiment the outside is metallised (for example with a thin spray coating) and grounded for electrical shielding from stray radiofrequency sources.

The protective layer 20 may be of any suitable thickness, 9 micrometres for example. The protective layer is provided for physical protection and optimally should have no or minimal effect on the performance of the first and second pyroelectric elements 14, 12.

In practice, the layers 12-20 may be bonded to one another by a suitable bonding or adhesive, preferably having non-matched characteristics. In the preferred embodiments, the glue has properties (acoustic etc.) that are substantially identical to the properties of the material layers on either side, as they are deposited from the material applied in solvent form. The glue layers can also be made conducting by doping with metallic flakes. The preferred glue layer only has an adhesive function, with the matching of the properties meaning that the sensitivity of the device can be maximised. In practical embodiments, the structure disclosed herein can be bonded together with a non-property matched glue. This is advantageously made as thin as possible to reduce losses, preferably just a few micrometres thick. In practice, an off-the shelf glue can be used that is adapted to bond together layers of PVDF and non-matched means in terms of acoustic impedance (Z) in relation to the (PVDF) layers. An example is a nitrile-rubber-based adhesive such as BOSTIK 1755 (diluted to 5 wt % with BOSTIK 6322 thinner). BOSTIK is a Registered Trade Mark.

In preferred embodiments, further thin layers may be disposed in intimate contact with the pyroelectric layers 12, 14 to dissipate the signal away more rapidly (essentially increasing thermal conductivity), thereby ensuring that the signal from the sensor 10 decays to background as quickly as possible (a factor which affects scanning speed as it dictates when the next firing of the transducer can be executed.

To summarise, in use of a preferred embodiment of the sensor:

An ultrasound wave arrives from the top of FIG. 1.

It passes through a top protective layer 20 essentially unchanged.

It passes through layer 12 to produce a first electrical signal by means of the pyroelectric effect. There is a small component of heating of the layer 12 by the ultrasound because the layer absorbs some energy, but this is small in comparison to heat generated by absorption in the absorbing backing 18. Thus, the level of the pyroelectric signal level generated by the layer 12 is small.

The wave passes through the electrically insulated spacer layer 16.

It then passes through layer 14 to produce a second electrical signal (essentially identical to the first one, just time delayed). Again, intrinsic attenuation or absorption in layer 16 is small, so the pyroelectric signal is small.

It then passes into the absorbing backing where it is immediately absorbed. The heat generated at the interface between layers 14 and 18 then conducts outwards through layer 16 to layer 12.

The useful output is taken as the difference between the two electrical signals.

The spacer layer 16 is electrically insulating to prevent the two layers 12 and 14 from shorting. The spacer layer 16 acts to keep the two pyroelectric layers 12, 14 close enough such that they see effectively the same vibration or background acoustic excitation, while maintaining sufficient distance to ensure that the pyroelectric layers 12, 14 generate significant differences in their pyroelectric responses.

Using short pulses enables the signals due to conducting heat from the first and second membranes to be distinguished in time. This is important in terms of acquiring data quickly.

Any other influences e.g. from the piezoelectric response of the membranes, affect the layers 12 and 14 equally.

The assembly 10 preferably includes a heat sink for removing heat such that there is no significant pyroelectric signal generated by the front membrane 12.

Referring now to FIGS. 3 to 6, these are graphs showing the performance characteristics of different natures of layers useful in determining the optimum structure for the sensor.

Figure 3:
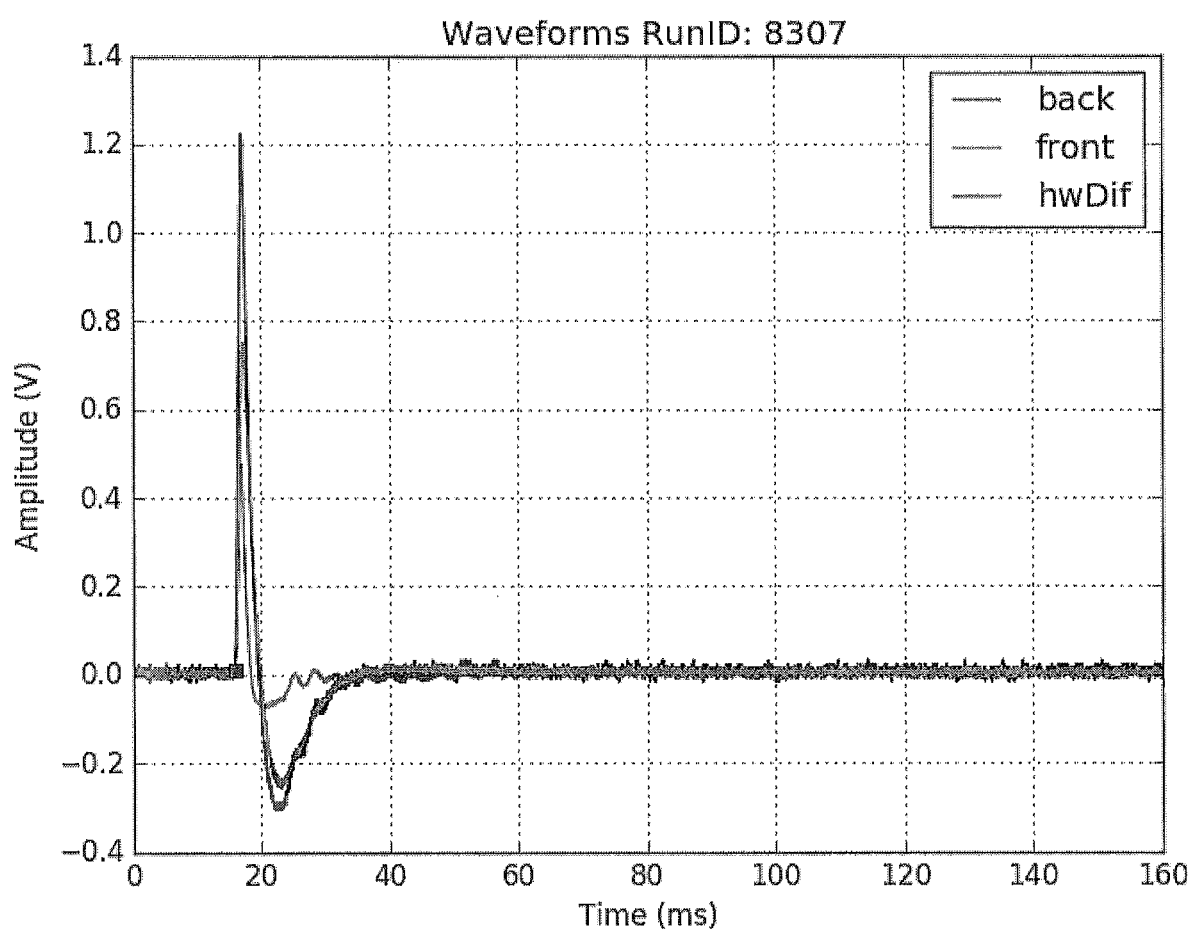
FIGS. 3 to 8 are graphs showing the performance characteristics of different natures of layers useful in determining the optimum structure for the sensor.

FIG. 3 is a direct measurement of the waveforms generated by a tri-laminar sensor as taught herein, showing those from PVdF1 (back) and PVdF2 (front), along with the difference. Ripples caused by background vibration can be seen on both electrodes but are effectively cancelled out by taking the differential signal (red of hwDif). These measurements were carried out in water. Through breast tissue, the arriving peak that needs to be measured is significantly reduced, by a factor of at least a 1000, making the peak <1 mV, significantly less than the noise ripple seen on the individual waveforms.

Figure 4:
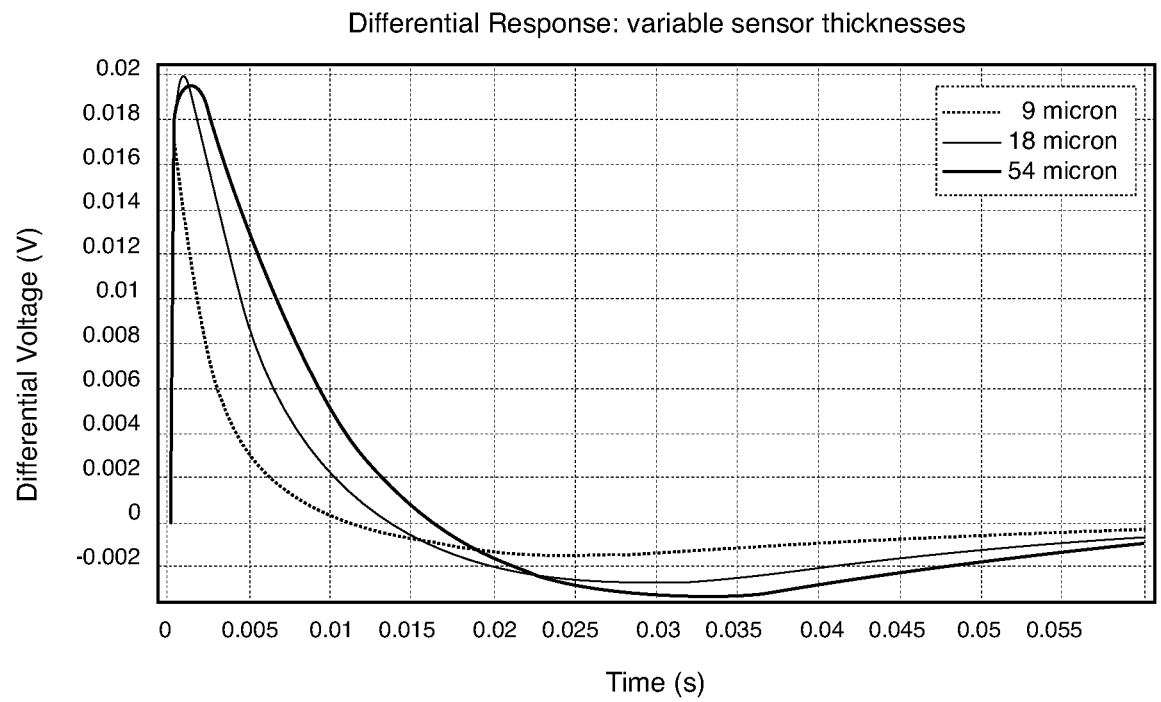

FIG. 4 shows the results of a theoretical model of the differential response of a tri-laminar sensor as taught herein in which the thickness of both electrodes are the same, but at three different nominal thicknesses. The voltages are not the same as FIG. 3 due to different voltage gain conditions on the electronics. The spacer thickness was 9 micrometres.

The effect of the varying the sensor thickness, for both sensors, shows the following changes in characteristics:

| Sensor thicknesses [microns] | Peak [V] | Time to peak [s] |
| --- | --- | --- |
| 9 | 0.0168 | 0.0010 |
| 18 | 0.0206 | 0.00173 |
| 54 | 0.0183 | 0.00204 |

Figure 5:
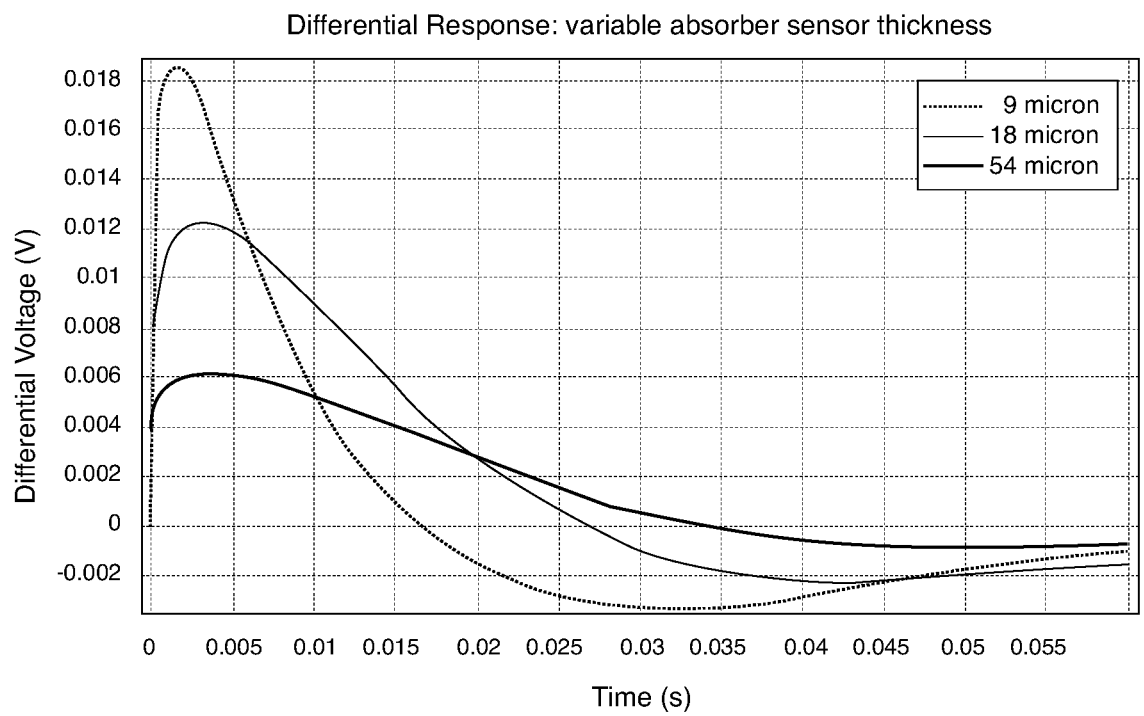

FIG. 5 is a series of graphs showing the effect on the signal of varying the thickness of the sensor 14 next to the absorber 18. It is possible to extract the following exemplary data from these graphs:

| Absorber sensor Thickness [microns] | Peak [V] | Time to peak [s] |
| --- | --- | --- |
| 9 | 0.0186 | 0.0185 |
| 18 | 0.0123 | 0.0038 |
| 54 | 0.0062 | 0.0041 |

Figure 6:
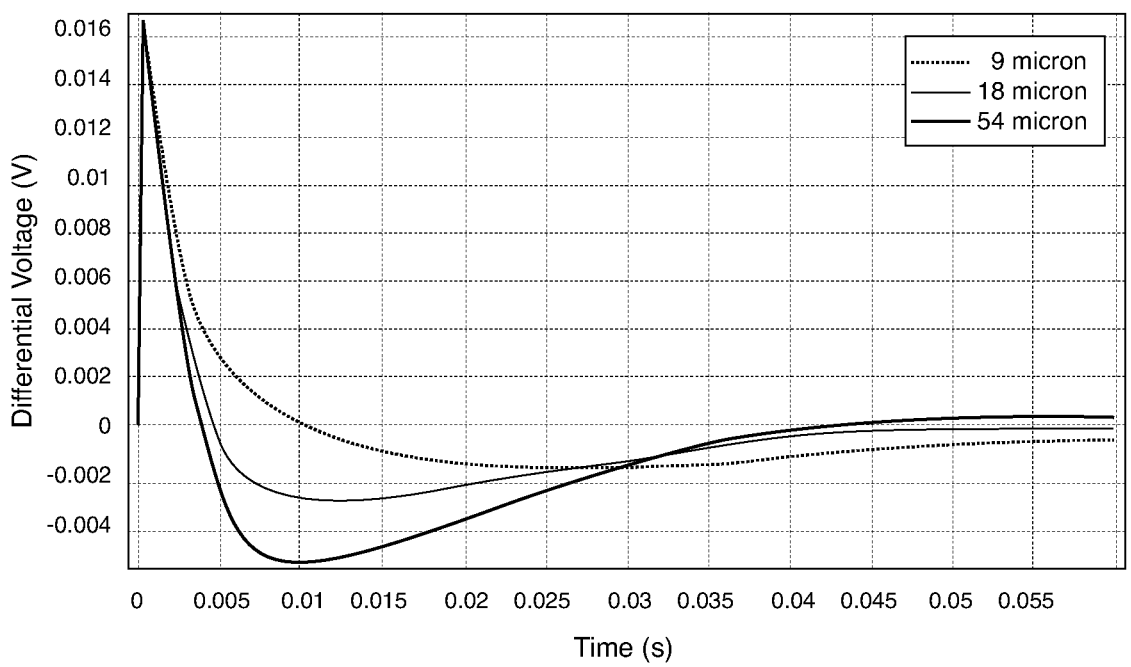

FIG. 6 is a series of graphs showing the effect on the signal by varying the thickness of the sensor 12 furthest from the absorber 18, so that is the sensor typically in contact with water. It is possible to extract the following exemplary data from these graphs:

| Water sensor Thickness [microns] | Peak [V] | Time to peak [s] |
| --- | --- | --- |
| 9 | 0.0167 | 0.0010 |
| 18 | 0.0162 | 0.0010 |
| 54 | 0.0155 | 0.0010 |

Figure 7:
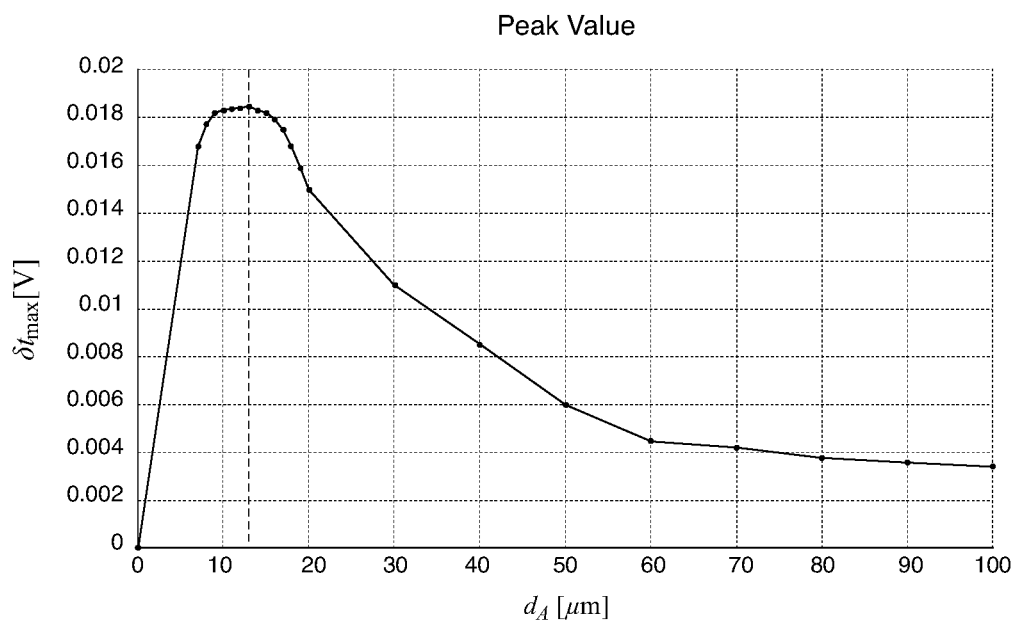

FIG. 7 is a graph of maximum (peak) sensor response with variable spacer thickness. Large impedance mismatches have two effects on diminishing the total signal. Firstly, the impedance mismatch inhibits wave propagation through to the absorber, so reduces the strength of the signal to the back face sensor. Secondly, the reflected wave is then re-absorbed by the front face sensor, so that the differential signal is further reduced.

Figure 8:
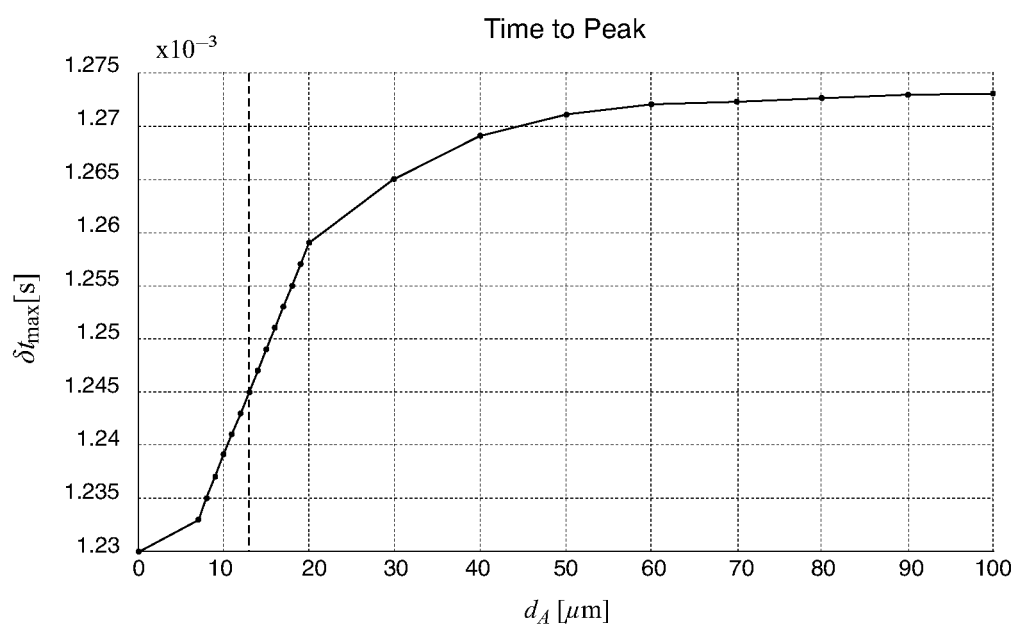

FIG. 8 shows the variation of time-to peak with spacer thickness.

The sensor array 10 increases signal to noise ratio coupled with an enhanced response speed that can significantly improve the performance of the sensor and imaging system compared to conventional structures.

A number of candidate materials for the spacer have been tested for commonly available materials. The optimum spacer is formed from a low attenuating, highly thermally conductive material with well-matched acoustic impedances. Ideally, the material would have the impedance of PVDF but the thermal properties of a metal.

The following example materials have been modelled, which have exhibited the following characteristics:

| Material | Density [kg/m3] | Speed of Sound [m/s] | Thermal Conductivity [W/m/K] | Attenuation [dB/m] |
| --- | --- | --- | --- | --- |
| PVDF | 1780 | 2560 | 0.19 | 1.63 |
| Copper | 8960 | 4760 | 400 | 1.71 |
| Aluminium | 2700 | 6374 | 237 | 1.71 |

-continued

| Material | Density [kg/m3] | Speed of Sound [m/s] | Thermal Conductivity [W/m/K] | Attenuation [dB/m] |
|---|---|---|---|---|
| Gold | 19300 | 3420 | 317 | 1.71 |
| PET | 1190 | 1950 | 0.18 | 1.63 |

The following metrics have been obtained for the different spacer materials, based on 27 micrometre thickness sensors, 9 micrometre thickness laminate, 9 micrometre thickness spacer

| Material | Peak [V] | Time to peak [s] |
|---|---|---|
| PVDF | 0.00139 | 0.00144 |
| Copper | 0.00147 | 0.00133 |
| Aluminium | 0.00164 | 0.00132 |
| Gold | 0.0283 | 0.0019 |
| PET | 0.0590 | 0.0012 |

Accurate computed tomographic reconstructions of the acoustic properties of tissue depends on achieving sufficient signal-to-noise performance. The preferred transducer structure, and its differential operation, means that coherent sources of this noise on both membranes will be effectively cancelled.

The solution provides ultrasound detection apparatus that involves:

1) a transducer as described, having two nominally identical membranes (the layers 12 and 14) placed as close together as possible. In practice (for (the layers 12 and 14) placed as close together as possible. In practice (for electrical independence), this involves separating the membranes 12 and 14 by inactive spacer layer 16 made as thin as possible. The spacer preferably has a thickness in the region of 9 micrometres and is of a polymer material which is electrically insulating but thermally conductive;

2) a detector unit operable to look at the difference in the responses of the two membranes 12 and 14 to incident ultrasound radiation, in which unwanted background vibration signals can be cancelled almost entirely, with subsequent improvements in signal-to-noise and the speed of response.

Figure 2:
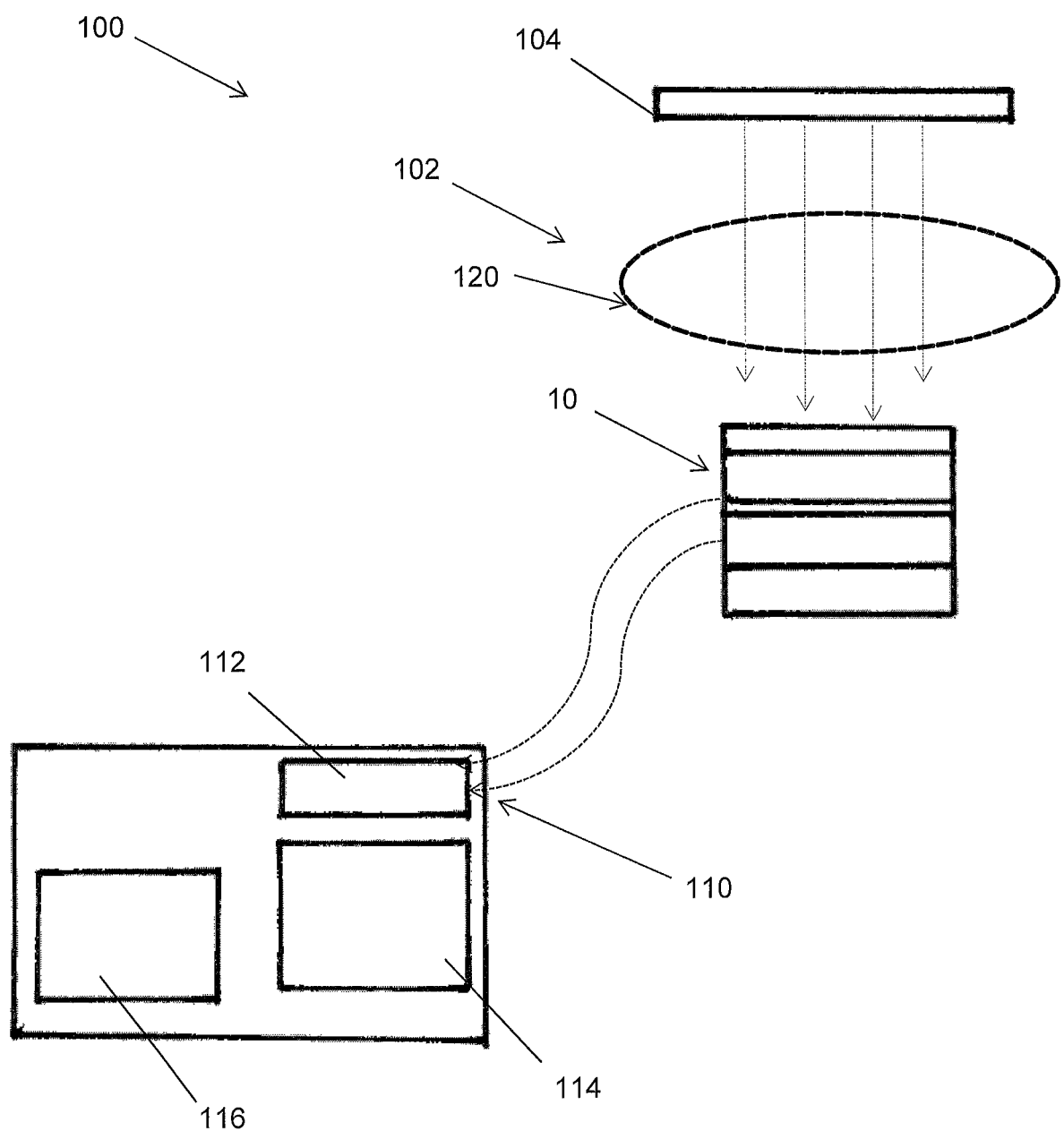
FIG. 2 shows in schematic form an embodiment of ultrasound detector apparatus according to the teachings herein.

An example of an ultrasound detection system 100 is shown in schematic form in FIG. 2. The tri-laminar sensor transducer 10 is shown disposed within a detection zone 102 of the apparatus, in which test element 120 can be positioned, which may for example be a human body part. A generator 104 of ultrasound energy is disposed so as to direct ultrasound towards the sensor array 10 through the test element 120. As is well known in the field, a suitable medium (gel or water for example) may be used to optimise coupling of the test element to the sensor array 10. In the Ultrasound Computed Tomography configuration, this medium will be water or similar as the generator of ultrasound 104 and sensor 10 will have to be rotated around the test element 120.

The apparatus also includes a processing unit 110, which comprises a detector unit 114 coupled through an input unit 112 to the first and second pyroelectric elements 14, 12 of the sensor array 10 and configured to derive a differential signal from the first and second pyroelectric elements 14, 12. A processor 116 is coupled to the detector unit 114 and is configured to generate a detection profile on the basis of the data extracted from first and second pyroelectric elements 14, 12.

The ultrasound detector can be used for a variety of imaging applications and is particularly suited to medical applications such as imaging for breast disease and other hard and soft tissue parts such as for testicular disease, bone illnesses, and so on. The array can be used in an ultrasound detector, a pyroelectric sensor apparatus, for ultrasound computed tomography (UCT), breast imaging and so on. The detector can also be used in non-medical applications, for example in the detection of structural characteristics such as structural or component cracks.

The skilled person will appreciate that the sensor device 10 can be used in non-ionising radiation based, non-compression (limits overlaps and resulting false negatives and false positives), 360° imaging methods, which are lower cost than MRI and DBT.

A UCT system using the sensor 10 is operator independent and can therefore enable use by lower skilled and cheaper staff. It can also be used for Quantitative Imaging (QI), which means that data can be compared directly across the population.

The intrinsically safe nature of ultrasound technology means that repeat scans can be made and the technology could be applied in wider non-hospital locations (such as GP surgeries, gyms and so on) as there are no ionising radiation protection issues. The ability to repeat scans means that the effect of drugs on tumour size and pathology can be followed at more regular and frequent intervals. QI and the ability to pool data, which can be compared in a common way across huge populations through deep learning or artificial intelligence, can significantly increase diagnostic power long-term, for establishing appropriate treatment pathways.

The sensor 10 disclosed herein can be used alongside other imaging methods, for instance as an adjunct to x-ray mammography, particularly useful for the diagnosis of breast disease in younger women, but also with other imaging methods providing complementary information, both conventional ultrasound and other techniques.

What is claimed is:

1. An ultrasonic sensor including first and second overlaying pyroelectric layers, an electrically insulating spacer layer disposed between the first and second pyroelectric layers thereby to separate electrically the first and second pyroelectric layers from one another, and an absorbing layer in direct contact with the first pyroelectric layer.

2. A sensor according to claim 1, wherein the first and second pyroelectric layers are respectively a measurement electrode and a reference electrode.

3. A sensor according to claim 1, wherein the spacer layer has a thickness between 1 and 100 micrometres.

4. A sensor according to claim 3, wherein the spacer layer has a thickness of substantially 9 micrometres.

5. A sensor according to claim 1, wherein the spacer is made of a polymer material.

6. A sensor according to claim 1, wherein the spacer is made of thermally conductive material.

7. A sensor according to claim 1, including at least one signal dissipating layer disposed in contact with at least one of the pyroelectric layers.

8. A sensor according to claim 1, including a heat sink coupled to the first pyroelectric layer for removing heat from said pyroelectric layer.

9. A sensor according to claim 1, wherein the first and second pyroelectric layers each have a thickness of between 1 and 60 micrometres.

10. A sensor according to claim 9, wherein the first and second pyroelectric layers each have a thickness of substantially 28 micrometres.

11. A sensor according to claim 5, wherein the first and second pyroelectric layers are made of polyvinylidene difluoride.

12. A sensor according to claim 11, wherein the first and second pyroelectric layers are made of poled polyvinylidene difluoride.

13. A sensor according to claim 12 wherein the spacer layer is made of unpoled polyvinylidene difluoride.

14. A sensor according to claim 5, wherein the spacer is made of polyethylene terephthalate, a polyester or polymethyl methacrylate.

15. Ultrasound detection apparatus including;
a generator of ultrasound energy;
at least one sensor according to claim 1;
a detector unit coupled to the first and second pyroelectric layers and configured to derive a differential signal from the first and second pyroelectric layers; and
a processor coupled to the detector unit and configured to generate a detection profile on the basis of the differential signal.

16. Ultrasound detection apparatus including:
a generator of ultrasound energy;
at least one ultrasound transducer comprising first and second overlaying layers made of poled polyvinylidene difluoride separated by an electrically insulating spacer layer of unpoled polyvinylidene difluoride, said first layer constituting a measurement electrode and said second layer constituting a reference electrode;
an absorbing layer in contact with said first layer;
a detector unit coupled to said first and said second layers and configured to derive a differential signal from the first and second pyroelectric layers; and
a processor coupled to the detector unit and configured to generate a detection profile on the basis of the differential signal.

\* \* \* \* \*

UNITED STATES PATENT AND TRADEMARK OFFICE
CERTIFICATE OF CORRECTION

PATENT NO. : 11,125,727 B2
APPLICATION NO. : 16/456147
DATED : September 21, 2021
INVENTOR(S) : Bajram Zeqiri Page 1 of 1

It is certified that error appears in the above-identified patent and that said Letters Patent is hereby corrected as shown below:

On the Title Page

Foreign application priority data should be included as follows:
--June 29, 2018 (GB) 1810751--

Signed and Sealed this
Eighth Day of July, 2025

Coke Morgan Stewart
*Acting Director of the United States Patent and Trademark Office*